(12) United States Patent
Cathier et al.

(10) Patent No.: US 10,925,677 B2
(45) Date of Patent: Feb. 23, 2021

(54) MEDICAL INTERVENTIONAL IMAGING DEVICE

(71) Applicant: KONINKLIJKE PHILIPS N.V., Eindhoven (NL)

(72) Inventors: Pascal Yves François Cathier, Asnières-sur-Seine (FR); Raoul Florent, Ville D'Avray (FR); Olivier Pierre Nempont, Suresnes (FR); Guillaume Julien Joseph Pizaine, Issy-les-Moulineaux (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/736,093

(22) PCT Filed: Jun. 23, 2016

(86) PCT No.: PCT/EP2016/064548
§ 371 (c)(1),
(2) Date: Dec. 13, 2017

(87) PCT Pub. No.: WO2016/207283
PCT Pub. Date: Dec. 29, 2016

(65) Prior Publication Data
US 2018/0177555 A1 Jun. 28, 2018

(30) Foreign Application Priority Data
Jun. 25, 2015 (EP) .................................. 15305994

(51) Int. Cl.
*A61B 34/20* (2016.01)
*G16H 30/20* (2018.01)
(Continued)

(52) U.S. Cl.
CPC ................ *A61B 34/20* (2016.02); *A61B 6/12* (2013.01); *G06F 19/321* (2013.01); *G16H 30/20* (2018.01);
(Continued)

(58) Field of Classification Search
CPC .. G16H 30/20; A61B 2090/376; A61B 6/485; A61B 6/12; A61B 34/20; A61B 6/00;
(Continued)

(56) References Cited

U.S. PATENT DOCUMENTS 5,560,352 A 10/1996 Heim
7,338,443 B1 3/2008 Tucker
(Continued)

FOREIGN PATENT DOCUMENTS

EP 1769771 A1 4/2007
EP 1839558 A1 * 10/2007 ......... G01N 21/6486
(Continued)

*Primary Examiner* — Dramos Kalapodas

(57) ABSTRACT

The present invention relates to an medical interventional imaging device (1) for monitoring an interventional procedure, the medical interventional imaging device (1) comprising: a temporary data buffer (10) configured to temporarily store medical interventional fluoroscopic image data; a signal processor (20) configured to detect if an abnormal state occurs during an intervention and to record an instant at which the abnormal state has occurred; and a permanent data storage (30) configured to permanently store at least a part of the medical interventional fluoroscopic image data stored temporarily before and/or at the recorded instant if the abnormal state is detected.

15 Claims, 2 Drawing Sheets

(51) Int. Cl.
*G06F 19/00* (2018.01)
*A61B 6/12* (2006.01)
*H04N 7/18* (2006.01)
*A61B 90/00* (2016.01)
*A61B 6/00* (2006.01)

(52) U.S. Cl.
CPC .............. *H04N 7/188* (2013.01); *A61B 6/485* (2013.01); *A61B 6/504* (2013.01); *A61B 2034/2065* (2016.02); *A61B 2090/376* (2016.02)

(58) Field of Classification Search
CPC ... A61B 18/1492; A61B 6/548; G06F 19/321; H04N 7/188
See application file for complete search history.

(56) References Cited

U.S. PATENT DOCUMENTS

| | | | |
|---|---|---|---|
| 8,489,554 B2 | 7/2013 | Xu | |
| 2003/0097077 A1* | 5/2003 | Morganroth | G16H 10/20 600/509 |
| 2007/0078678 A1* | 4/2007 | DiSilvestro | G06Q 50/22 705/2 |
| 2007/0118054 A1* | 5/2007 | Pinhas | A61B 5/1104 600/587 |
| 2007/0276270 A1* | 11/2007 | Tran | A61B 5/002 600/508 |
| 2011/0314310 A1 | 12/2011 | Rajasekhar | |
| 2012/0116179 A1 | 5/2012 | Drew | |
| 2014/0081659 A1 | 3/2014 | Nawana | |
| 2014/0267710 A1* | 9/2014 | Asada | G08B 3/10 348/143 |
| 2014/0316269 A1 | 10/2014 | Zhang | |
| 2014/0365244 A1* | 12/2014 | Lee | G06F 19/321 705/3 |
| 2016/0081608 A1* | 3/2016 | Lovoi | A61B 5/4064 600/483 |

FOREIGN PATENT DOCUMENTS

| | | | | |
|---|---|---|---|---|
| EP | 1839558 A1 | 10/2007 | | |
| JP | 2005253801 A | 9/2005 | | |
| JP | 2005253801 A | * 9/2005 | .............. | A61B 6/00 |
| JP | 2008302041 A | 12/2008 | | |
| JP | 2008302041 A | * 12/2008 | ............ | A61B 6/548 |
| JP | 2010088803 A | * 4/2010 | | |
| JP | 2010088803 A | 4/2010 | | |
| JP | 2015053133 A | * 3/2015 | ............ | F21S 41/275 |
| JP | 2015054133 A | 3/2015 | | |
| WO | 200013741 A2 | 3/2000 | | |
| WO | 2006116198 A2 | 11/2006 | | |
| WO | WO-2006116198 A2 | * 11/2006 | .............. | A61N 1/06 |
| WO | 2007067323 A2 | 6/2007 | | |
| WO | WO-2007067323 A2 | * 6/2007 | ............ | G06T 19/00 |

* cited by examiner

MEDICAL INTERVENTIONAL IMAGING DEVICE

CROSS-REFERENCE TO PRIOR APPLICATIONS

This application is the U.S. National Phase application under 35 U.S.C. § 371 of International Application No. PCT/EP2016/064548, filed on Jun. 23, 2016, which claims the benefit of European Patent Application No. 15305994.4, filed on Jun. 25, 2015. These applications are hereby incorporated by reference herein.

FIELD OF THE INVENTION

The present invention relates to the field of interventional medical imaging systems. In particular, the present invention relates to a medical interventional imaging device for monitoring an interventional procedure, a medical data storage system, and a corresponding method.

BACKGROUND OF THE INVENTION

Various storage mechanisms and various data storage strategies are used in systems supporting or providing imaging functions during medical interventions, such as systems used for interventional X-ray imaging assisted or guided medical interventions. In those systems, only particular data such as high-exposure images used for diagnosis are automatically stored, for instance images as gathered from angiography.

Live data, for instance, images used for navigation and device placement are low-dose images, for instance, fluoroscopy, and these images are normally not stored, because this would require excess storage volumes.

SUMMARY OF THE INVENTION

There may be a need to improve medical interventional imaging devices for monitoring an interventional procedure.

This need is met by the subject-matter of the independent claims. Further exemplary embodiments are evident from the dependent claims and the following description.

The present invention relates to a medical interventional imaging device for monitoring an interventional procedure. The medical interventional imaging device comprises a temporary data buffer configured to temporarily store medical interventional fluoroscopic image data.

The medical interventional imaging device further comprises a signal processor configured to detect if an abnormal state occurs during an intervention and to record an instant at which the abnormal state has occurred.

Further, the medical interventional imaging device comprises a permanent data storage configured to receive and store at least a part of the temporarily stored medical interventional fluoroscopic image data before and/or at the recorded instant upon detection of the abnormal state.

The term "instant" as used by the present invention may refer to a moment in time, for instance a time point, it may also be defined as a short time period, for instance, as a period of less than a certain amount of ms or µs, for instance a time period of less than 100 ms, or less than 10 ms or 1 ms or 100 µs. In other words, if the abnormal state is detected, at least a part of the medical interventional fluoroscopic image data stored temporarily in a time period from 100 ms before the moment of detection till up to the moment of detection may be then—at least partially—permanently stored, that is, transferred or copied from the temporary data storage into the permanent data storage.

The term "temporarily" or "temporarily storing" as used by the present invention may refer to provisionally storing of data or to an interim data storing during an interventional procedure, in contrast to storing data more permanently. In this respect, "permanent" storing is understood to mean storing at least until after completion of an interventional procedure, so that the interventional image data in permanent storage may be reviewed and analyzed in retrospect.

In other words, the present invention provides an adaptive and conditional data storing, for instance live image storing such as fluoroscopy runs, in order to avoid overkilling storage demand that this would entail. For the case that an interventional procedure fails or reveals an abnormal situation, image data stored in permanent data storage would enable precious post procedure analysis.

When, during the medical intervention, any deviation from the nominal or planned situation is detected, all or a selected part of the streamed and buffered medical interventional fluoroscopic image data in temporary storage is transferred into permanent storage, preferably together with all or a selected part of the subsequent data pertaining to the ongoing intervention.

The deviation from a normal situation, the abnormal state occurring during the medical intervention, may be detected by analysis of the performed clinical workflow and comparison of the performed clinical workflow to a planned or scheduled clinical workflow. In other words, it is determined, firstly, if any divergences occurred in the performed clinical workflow with respect to the intended workflow and, if so, what type(s) of divergences. Then it may be determined whether these divergences are of interest for (an outcome of) this interventional procedure, when or why they occur during the procedure, and which fluoroscopic images are relevant and should be saved permanently for later review.

The interventional context may assign certain fluoroscopic images that are relevant for the interventional procedure and may relate divergences of the scheduled clinical workflow to certain fluoroscopic images which then may be reviewed and analyzed in more detail or which then may be stored with a higher priority.

The permanently stored material can then be replayed and analyzed at a later stage or even during the intervention in order to determine, for instance, what went wrong or in other words which entity failed during the interventional procedure, when the entity failed during the interventional procedure, why the entity failed, and possibly how to overcome similar situations in the future, e.g. in future interventional procedures.

According to a further, second aspect of the present invention, a medical data storage system is provided, the medical data storage system comprising a medical interventional imaging device according to the first aspect of the present invention or according to any implementation form of the first aspect of the present invention.

According to a further, third aspect of the present invention, a method for providing medical interventional image data with a medical interventional imaging device is provided, the method comprising the steps of:

temporarily storing medical interventional fluoroscopic image data;

detecting if an abnormal state in the intervention has occurred and recording the instant at which such state has occurred; and transferring at least a part of the medical interventional fluoroscopic image data stored temporarily before and/or at the instant to a permanent data storage upon a detection of the abnormal state.

In other words, the medical interventional fluoroscopic image data, which is transmitted to the permanent data storage if the abnormal state is detected, may comprise medical interventional fluoroscopic image data that had been buffered before the abnormality has been detected. This previously performed buffering may be performed with medical interventional fluoroscopic image data temporarily stored in a non-permanent buffer.

According to an exemplary embodiment of the present invention, the signal processor is configured to detect the occurring of the abnormal state based on a time period needed for a given interventional sub-procedure deviating from a scheduled time period for the interventional sub-procedure. This advantageously provides prognostics and analysis of the implications of interventional procedures in patients. In other words, the signal processor is configured to detect a time period needed for a given interventional sub-procedure deviating from a scheduled time period for that interventional sub-procedure, and then to decide if an abnormal event occurred based on this detection. In other more general words, the signal processor is configured to detect a tangible quantity, and then the signal processor is configured to output a decision.

The term "interventional sub-procedure" as used by the present invention may refer to a part or a step of an intervention, for instance, opening of the breastbone, or positioning of a suprapubic catheter, or sealing of a cavity.

According to an exemplary embodiment of the present invention, the signal processor is configured to detect the occurring of the abnormal state based on a withdrawal of an interventional device without a scheduled deployment of the interventional device having taken place. Again in more general words, the signal processor is configured to detect an event such as the refraction of the interventional device, for example a stent, which was not supposed or planned to be retracted, In this example, having corresponding image data of the retraction, and optionally the final stage of the attempted deployment, available in permanent storage may help in obtaining an improved analysis of potential causes of failures of interventional procedures in patients.

According to an exemplary embodiment of the present invention, the signal processor is configured to detect the occurring of the abnormal state based on a repeated deployment of an interventional device. The tangible quantity here corresponds to a number of deployments of the interventional device. A threshold for deployments of the interventional device may be defined, indicating an abnormal state if the threshold is exceeded. As an example, such abnormal state may be indicative of a failure in properly deploying the interventional device. In this example, having corresponding image data available in permanent storage may help in obtaining a precise understanding of what went wrong during the interventional procedure and allows determining how this could have been avoided.

According to an exemplary embodiment of the present invention, the signal processor is configured to detect the occurring of the abnormal state based on a use of an alternate, secondary interventional device after using a primary interventional device. This advantageously provides prognostics and analysis of the implications of interventional procedures in patients.

According to an exemplary embodiment of the present invention, the signal processor is configured to detect the occurring of the abnormal state based on a parameter of the medical interventional imaging device or of a further interventional device used during the interventional procedure. This advantageously provides prognostics and analysis of the implications of interventional procedures in patients. Further this provides a precise understanding of what went wrong during the interventional procedures and allows determining how this could have been avoided.

According to an exemplary embodiment of the present invention, a parameter of an X-ray imaging device may be a range of angiographic viewing angles for an X-ray angiography, or may be a resolution, or X-ray exposure times used for X-ray angiography or X-ray imaging.

The term "repeated deployment" as used by the present invention may refer to a number of deployments above a certain threshold value, for instance, the threshold value is set to more than two, if the device is then three-times deployed, a repeated deployment is given.

The term "primary interventional device" as used by the present invention may refer to an interventional device which is used for a certain task. The term "secondary interventional device" as used by the present invention may refer to another interventional device which is used for the same or a similar task as the primary interventional device. In other words, from using the second interventional device, the signal processor may determine that the deployment of the primary interventional device was not successful.

An interventional device may include, without limitation, an endoscope or a cystoscope or a surgical instrument or an injection needle or a catheter.

According to an exemplary embodiment of the present invention, the signal processor is configured to detect the occurring of the abnormal state based on interventional data.

The term "interventional data" as used by the present invention may refer to diagnostic data of a patient or any data describing the operation of a device used during the intervention.

According to an exemplary embodiment of the present invention, the signal processor is configured to detect the abnormal state based on
  a signal filtering of the interventional data; and/or on
  a classification of the interventional data; and/or on
  a pattern recognition of the interventional data.
This advantageously provides a quality control of surgical and interventional procedures.

The term "classification" as used by the present invention may be defined as categorizing of data for providing an effective analysis of any kind of data.

The term "pattern recognition" as used by the present invention may refer to a machine learning technique that focuses on the recognition of patterns and regularities in data.

According to an exemplary embodiment of the present invention, the signal processor is configured to detect the occurring of the abnormal state based on interventional fluoroscopic image data.

According to an exemplary embodiment of the present invention, the signal processor is configured to detect the abnormal state based on
  a signal filtering of the interventional fluoroscopic image data; and/or on
  a classification of the interventional fluoroscopic image data; and/or on
  a pattern recognition of the interventional fluoroscopic image data. This advantageously provides an improved analysis of potential causes of failures of interventional procedures in patients as detectable in the interventional fluoroscopic image data.

According to an exemplary embodiment of the present invention, the signal processor is configured to detect the occurring of the abnormal state based on the interventional data in form of diagnostic data or in form of system data of the medical interventional imaging device or of a further interventional device used during the intervention. This advantageously also improves the analysis of the interventional procedure performance.

According to an exemplary embodiment of the present invention, the permanent data storage is a hard disk device. The hard disk device may be configured to permanently store at least a part of the interventional fluoroscopic image data. Advantageously this improves the analysis of the interventional procedure performance, too.

A computer program performing the method of the present invention may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The present invention can be implemented in digital electronic circuitry, or in computer hardware, firmware, software, or in combinations thereof, e.g. in available hardware of a medical device or in new hardware dedicated for processing the methods described herein.

These and other aspects of the present invention will become apparent from and be elucidated with reference to the embodiments described hereinafter.

BRIEF DESCRIPTION OF THE DRAWINGS

A more complete appreciation of the present invention and the attendant advantages thereof will be more clearly understood with reference to the following schematic drawings, which are not to scale, wherein.

DETAILED DESCRIPTION OF EMBODIMENTS

Figure 1:
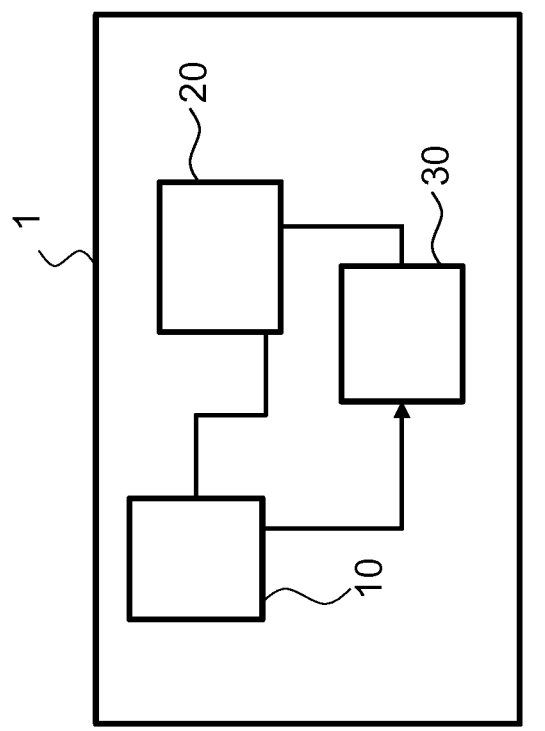
FIG. 1 shows a schematic diagram of a medical interventional imaging device according to an exemplary embodiment of the present invention.

The illustration in the drawings is purely schematic and does not intend to provide scaling relations or size information. In different drawings or figures, similar or identical elements are provided with the same reference numerals. Generally, identical parts, units, entities or steps are provided with the same reference symbols in the description.

Advantageously, a mechanism is provided to conditionally store live data when abnormal situations occur. This avoids data volume explosion, only those interventions which went wrong are concerned, while offering complete live data storing for abnormal interventions.

The medical interventional imaging device 1 may provide that, when any deviation from the nominal situation of an ongoing medical intervention is diagnosed, all the data contained in a volatile storage may be transferred or copied into permanent storage, together with all the subsequent data pertaining to the current intervention.

In an example, only parts of the data contained in the volatile storage in form of the temporary data buffer 10 may be permanently stored. The stored material can then be replayed and analyzed at a later stage or for instance also during the intervention in order to determine what went it wrong, why it went wrong, and possibly how to overcome similar situations in the future.

The medical interventional imaging device 1 may allow improving the intervention protocol, in particular improving the intervention protocol due to a better understanding, based on the data in permanent storage, what could have gone wrong in a former or previously performed interventional procedure.

The medical interventional imaging device 1 may be configured to filter and store the most relevant data from a large amount of interventional data.

The medical interventional imaging device 1 may be configured to store interventional images when a predefined event occurs, the predefined event relating to an abnormality of an interventional procedure.

The medical interventional imaging device 1 may be configured to enable storing images of large size—up to several megabytes or gigabytes in form of single images or continuous image sequences—and the medical interventional imaging device 1 may be configured to provide information to the interventionist by reviewing specific moments or actions of the interventional procedure.

FIG. 1 shows a schematic diagram of a medical interventional imaging device 1 according to an exemplary embodiment of the present invention.

The medical interventional imaging device 1 for monitoring an interventional procedure comprises a temporary data buffer 10, a signal processor 20, and a permanent data storage 30.

The medical interventional imaging device 1 for monitoring an interventional procedure may be configured to monitor an interventional procedure. Monitoring the interventional procedure may comprise monitoring all or at least a pre-defined part of the parameters of the deployed devices and all or at least a pre-defined part of diagnostic data as available.

The medical interventional imaging device 1 for monitoring an interventional procedure may be an X-ray imaging device or an ultrasonic imaging device or an imaging device configured to provide image information in terms of image data during an interventional procedure.

The temporary data buffer 10 is configured to temporarily store medical interventional fluoroscopic image data or image data. The medical interventional image data may be recorded during an interventional procedure by fluoroscopic imaging devices.

The signal processor 20 is configured to detect if an abnormal state in an intervention has occurred and to record an instant at which the abnormal state has occurred. Further, the signal processor 20 is configured to record the time at which the abnormal state occurs. The abnormal state refers to the interventional procedure itself, e.g. a deviation in workflow or schedule, or to any device used during the interventional procedure, e.g. a failed or sub-optimal deployment of such device.

The permanent data storage 30 is configured to store at least a part of—in other words all or a part of—the temporarily stored medial interventional fluoroscopic image data.

For this purpose, upon a detection of an abnormal state by the signal processor 20, image data is transferred from the temporary data buffer 10 to the permanent data storage 30, which is configured to receive the image data. The medial interventional fluoroscopic image data may also be called interventional fluoroscopic image data or image data in the following.

The permanently storing of the interventional fluoroscopic image data may be performed at the recorded instant if the abnormal state is detected, temporarily stored image data stored before and/or at the recorded instant may then be permanently saved. The data transmission of the medical interventional fluoroscopic image data from the temporary data buffer 10 to the permanent data storage 30 may be performed as indicated by the arrow in FIG. 1.

According to an exemplary embodiment of the present invention, the signal processor 20 is configured to detect the occurring of the abnormal state based on interventional data.

The interventional data may comprise diagnostic data of a patient or any data describing the status or the operation of a device, for instance of an interventional device used during the intervention, e.g. of the medical interventional imaging device 1 or of any other interventional device deployed.

According to an exemplary embodiment of the present invention, the signal processor 20 is configured to detect the occurring of the abnormal state based on a time period needed for a given interventional sub-procedure deviating from a scheduled time period for the interventional sub-procedure.

This may be provided if the interventional context is known beforehand by the medical interventional imaging device 1 for monitoring an interventional procedure. Various kinds of sub-procedures for a specific interventional context may be defined by the medical interventional imaging device 1 and expected time periods for these sub-procedures may be pre-defined by the medical interventional imaging device 1 for monitoring an interventional procedure.

According to an exemplary embodiment of the present invention, the signal processor 20 may be configured to detect the occurring of the abnormal state based on imaging system parameters (e.g. C-arm acquisition geometry, position) or based on device-specific detections or based on a "state" of an interventional device (e.g. a valve not deployed or deployed) in the fluoroscopic images. The signal processor 20 may be further configured to subsequently perform a classification of the fluoroscopic images.

According to an exemplary embodiment of the present invention, the signal processor 20 is configured to detect the occurring of the abnormal state based on a withdrawal of an interventional device without deployment of the interventional device. According to an exemplary embodiment of the present invention, the interventional device may be a stent, any kind of valve prostheses, or a coil or another device.

According to an exemplary embodiment of the present invention, the signal processor 20 may be configured to detect the abnormal state based on a low-level filtering and/or device-specific detection through filtering or pattern recognition algorithms of the interventional data or of the medical interventional fluoroscopic image data.

According to an exemplary embodiment of the present invention, the signal processor 20 is configured to detect the occurring of the abnormal state based on a: a repeated deployment of an interventional device.

A repeated deployment of an interventional device may be detected also by another, second interventional device, whose presence or activation is required for each and every deployment of the first interventional device.

According to an exemplary embodiment of the present invention, the repeated deployment may also require a higher-level model of the interventional procedure, e.g. the interventional context. For instance, modeling the interventional procedure may comprise distinguishing between deployed and non-deployed states of the interventional devices. These models may be originated from low-level image filtering and/or machine learning techniques.

According to an exemplary embodiment of the present invention, a use of an alternate, secondary interventional device after using a primary interventional device may be considered for the detection of an abnormality by the signal processor 20.

According to an exemplary embodiment of the present invention, the signal processor 20 may be configured to detect the abnormal state based on a parameter of the medical interventional imaging device or of an interventional device used during the interventional procedure.

The parameter of the interventional device may be a parameter of a vital sign. The interventional device may be a device with integrated sensors (e.g. pressure catheters), wherein the parameter may be a blood pressure. The parameter of the interventional device may be a non-planned or unusual C-arm position parameter.

As an example of abnormality detection as performed by the signal processor 20, the following procedure is presented:

During a transcatheter aortic valve implantation, abbreviated TAVI, procedure, a monitoring of the deployment of the valve to be implantated is performed. An accurate positioning of the valve is crucial to avoid paravalvular regurgitations and to ensure a safe outcome for the patient.

Once the valve prosthesis has been accurately positioned, it may be deployed within a few—up to 40—seconds in a specific mode. After deployment, the interventionist may perform an additional angiography with contrast medium to assess the final position of the valve relative to the aortic root.

If the position differs from what has been planned, for instance by more than a threshold of 5 millimeters or 2 millimeters or 0.5 millimeters, the interventionist may decide to implant a second prosthesis inside the first one or to correct the position of the current device (if the choice of the device allows for repositioning). The position may be thus assessed visually first. If there is no clear evidence, a catheter measuring blood pressure may be used in a second time.

As a further example of abnormality detection performed by the signal processor 20, the signal processor 20 may detect an abnormal valve deployment. The detection of the abnormal valve deployment can be performed only once the pacemaker is activated on a restricted span of time, which is possible if the interventional context of the procedure is known.

The detection of the abnormal valve deployment may be detected by the signal processor 20 due to the following aspects:

if an unusually long period of time is required for the deployment, which is detected by monitoring a parameter of an interventional device which is to be deployed (e.g. a pacemaker signal) by the signal processor 20;
AND/OR
if several deployments of the same valve are detected by the signal processor 20, for instance by detecting the valve in the fluoroscopic images (low-level filters and template matching algorithms) and checking how its width evolves. In the case of an Edward Sapiens XT valve, also multiple inflations of the balloon may be considered by the signal processor 20, which is mandatory to deploy the valve;

AND/OR if a second valve is deployed within the first one, which is detected by the signal processor 20 if several prostheses are identified in the fluoroscopic images;

AND/OR if the measurements from the pressure catheter indicate the presence of a paravalvular regurgitation and this is detected by the signal processor 20.

Once the "abnormal valve deployment" event is detected by the signal processor 20, the following subsequent actions may be performed by the medical interventional imaging device 1:

The medical interventional imaging device 1 may be configured to dump all or at least a part of the fluoroscopic images present in the temporary data buffer 10 into the permanent data storage 30 once the abnormal valve deployment event is detected by the signal processor 20.

According to an exemplary embodiment of the present invention, the medical interventional imaging device 1 for monitoring an interventional procedure may be configured to permanently store only a part of the fluoroscopic images present in the temporary buffer in form of the temporary data buffer 10, since not all data concern the valve deployment stage.

According to an exemplary embodiment of the present invention, knowing what type of abnormality was detected, the medical interventional imaging device 1 may be configured to permanently store data relevant to this particular abnormality for the last X minutes. For instance, for the last 3 minutes before the abnormality was detected or for the last 20 seconds before the abnormality was detected, the medical interventional fluoroscopic images relevant to this particular abnormality may be permanently stored.

According to an exemplary embodiment of the present invention, knowing what type of abnormality was detected, the medical interventional imaging device 1 may be configured to permanently store data in form of fluoroscopic images acquired with the C-arm system positioned at the same angle/position (it is common practice that the interventionist uses a single C-arm position for the whole placement/deployment).

Additionally, for the rest of the procedure, the medical interventional imaging device 1 may be configured to bypass the temporary storage and may route all upcoming fluoroscopic images directly to the permanent storage 30.

The diagnostic data may comprise data from electrocardiography, abbreviated ECG or EKG, i.e. the process of recording the electrical activity of the heart over a period of time using electrodes placed on a patient's body. ECG or EKG data is reflective of an abnormal situation.

The diagnostic data may comprise vital signs of the patient as recorded during an interventional procedure.

The term vital signs as used by the present invention may refer to any parameters that are used to measure the body's basic functions. These measurements may be taken to help assessing the general physical health of a person, give clues to possible diseases, and may show progress toward recovery. The normal ranges for a person's vital signs may vary with age, weight, gender, and overall health.

Examples of vital signs may include, but not limited to: body temperature, blood pressure, pulse or heart rate, and breathing rate, also called respiratory rate.

According to an exemplary embodiment of the present invention, the temporary data buffer 10 may be, for instance, a volatile storage in form of a RAM drive. The volatile storage may be a computer memory that uses electrical power to maintain the stored information.

According to an exemplary embodiment of the present invention, the size of the permanent data storage 30 may be adapted to a time period needed for the interventional procedure.

According to an exemplary embodiment of the present invention, the permanent data storage 30 may be a memory card or a flash card in form of an electronic flash memory data storage device used for storing digital information, e.g. the medical interventional fluoroscopic image data.

According to an exemplary embodiment of the present invention, the signal processor 20 may be configured to detect the occurring of the abnormal state based on a time period needed for a given interventional sub-procedure deviating from a scheduled time period for the interventional sub-procedure.

Further, the signal processor 20 may be configured to detect the occurring of the abnormal state based on a withdrawal of an interventional device without deployment of the interventional device or on a repeated deployment of an interventional device or on a use of an alternate, secondary interventional device after using a primary interventional device or on a parameter of the medical interventional imaging device 1.

In other words, the medical interventional imaging device 1 may be configured to provide information and to store needed information to improve the intervention protocol, in particular to better understand what could have gone wrong in a former intervention.

According to an exemplary embodiment of the present invention, the medical interventional imaging device 1 is configured to filter and store the most relevant data from a large amount of interventional image data or interventional fluoroscopic image data, wherein the most relevant data is determined to be represented by data which is more relevant than a predefined threshold value of relevance. In other words, a relevance value may be assigned to the acquired data.

According to an exemplary embodiment of the present invention, the medical interventional imaging device 1 for monitoring an interventional procedure is configured to store interventional images when a predefined event occurs, the predefined event relating to an abnormal situation of an interventional procedure, for instance, related to the patient, the interventional procedure or any interventional device used during or for the interventional procedure.

Figure 2:
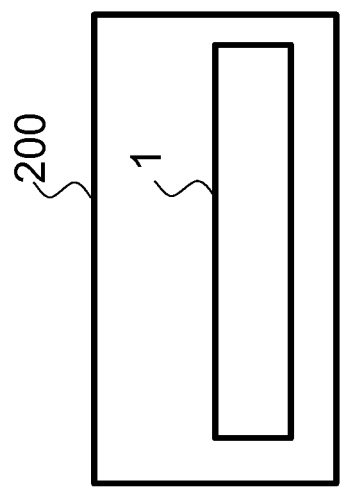
FIG. 2 shows a schematic diagram of a medical data storage system according to an exemplary embodiment of the present invention.

FIG. 2 shows a schematic diagram of a medical data storage system according to an exemplary embodiment of the present invention.

According to an exemplary embodiment of the present invention, a medical data storage system 200 may comprise a medical interventional imaging device 1.

According to an exemplary embodiment of the present invention, the medical data storage system 200 may be used in connection with an X-ray medical imaging system or with an ultrasonic medical imaging system or with an endoscopic system.

According to an exemplary embodiment of the present invention, also further medical intervention procedure supporting systems may be used in connection with the medical interventional imaging device 1, where live data storage is limited because of the overkilling storage volumes involved.

The medical imaging device 1 for monitoring an interventional procedure may be a medical imaging workstation or an X-ray medical imaging system.

Figure 3:
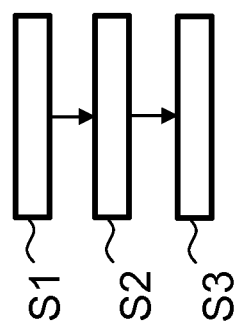
FIG. 3 shows a schematic diagram of a flowchart diagram of a method for providing medical interventional image data with a medical interventional imaging system according to an exemplary embodiment of the present invention.

FIG. 3 shows a schematic diagram of a flowchart diagram of a method for providing medical interventional image data with a medical interventional imaging device according to an exemplary embodiment of the present invention.

The method for providing medical interventional image data with a medical interventional imaging device may comprise the following steps:

As a first step a) of the method, temporarily storing S1 medical interventional fluoroscopic image data may be conducted.

As a second step b) of the method, detecting S2 if an abnormal state occurs during the intervention and recording the instant at which such state has occurred may be conducted.

As a third step c) of the method, sending S3 the medical interventional fluoroscopic image data stored temporarily before and/or at the instant to a permanent data storage may be conducted if the abnormal state is detected.

It has to be noted that embodiments of the present invention are described with reference to different subject-matters. In particular, some embodiments are described with reference to method type claims whereas other embodiments are described with reference to device type claims.

However, a person skilled in the art will gather from the above and the foregoing description that, unless otherwise notified, in addition to any combination of features belonging to one type of the subject-matter also any combination between features relating to different subject-matters is considered to be disclosed with this application. However, all features can be combined providing synergetic effects that are more than the simple summation of these features.

While the present invention has been illustrated and described in detail in the drawings and the foregoing description, such illustration and description are to be considered illustrative or exemplary and not restrictive; the present invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A medical imaging device for storing medical image data during an interventional procedure, comprising:
   a temporary data buffer configured to temporarily store medical interventional fluoroscopic image data;
   a signal processor configured to detect if an abnormal state in the interventional procedure has occurred, and to record an instant at which the abnormal state has occurred; and
   a permanent data storage configured to receive and store at least a part of the temporarily stored medical interventional fluoroscopic image data stored before and/or at the recorded instant upon detection of the abnormal state,
   wherein the signal processor is configured to determine a type of the detected abnormal state in the interventional procedure, and
   to cause the permanent data storage to vary the amount of stored data based on:
   time duration of the medical relevance of interventional fluoroscopic image data temporarily stored before the recorded instant in dependence on the determined type of the detected abnormal state;
   a result decision determined from the fluorescent data;
   according to a result relevance factor compared to a threshold value; and
   a predefined intervention event.

2. The medical interventional imaging device according to claim 1,
   wherein the signal processor is configured to detect the occurring of the abnormal state based on a time period needed for a given interventional sub-procedure deviating from a scheduled time period for the interventional sub-procedure.

3. The medical interventional imaging device according to claim 1,
   wherein the signal processor is configured to detect the occurring of the abnormal state based on a withdrawal of an interventional device without deployment of the interventional device.

4. The medical interventional imaging device according to claim 1,
   wherein the signal processor is configured to detect the occurring of the abnormal state based on a repeated deployment of an interventional device.

5. The medical interventional imaging device claim 1,
   wherein the signal processor is configured to detect the occurring of the abnormal state based on a use of an alternate, secondary interventional device after using a primary interventional device.

6. The medical interventional imaging device claim 1,
   wherein the signal processor is configured to detect the occurring of the abnormal state based on a parameter of the medical interventional imaging device or of an interventional device used during the interventional procedure.

7. The medical interventional imaging device claim 1,
   wherein the signal processor is configured to detect the occurring of the abnormal state based on interventional data.

8. The medical interventional imaging device according to claim 7,
   wherein the signal processor is configured to detect the occurring of the abnormal state based on the interventional data in form of:
   diagnostic data; and/or in form of
   system data of the medical interventional imaging device or of an interventional device used during the intervention.

9. The medical interventional imaging device according to claim 8,
   wherein the signal processor is configured to detect the occurring of the abnormal state based on interventional fluoroscopic image data.

10. The medical interventional imaging device according to claim 1,
    wherein the permanent data storage is a hard disk device.

11. A medical data storage system comprising:
    a medical interventional imaging device according to claim 1.

12. A method for providing medical interventional image data with a medical imaging device during a medical intervention, the method comprising the steps of:

temporarily storing medical interventional fluoroscopic image data;
detecting if an abnormal state in the medical intervention has occurred;
determining a type of the detected abnormal state in the interventional procedure and recording an instant at which such state has occurred; and
transferring at least a part of the temporarily stored medical interventional fluoroscopic image data stored before and/or at the instant to a permanent data storage if the abnormal state is detected, said part varying in amount, based on time duration of the medical relevance of interventional fluoroscopic image data temporarily stored before the recorded instant in dependence on the determined type of the detected abnormal state;
a result decision determined from the fluorescent data, according to a result relevance factor compared to a threshold value and a predefined intervention event.

13. The method according to claim 12,
wherein the step of detecting if an abnormal state in the intervention has occurred comprises evaluating one or more of:

a time period needed for a given intervention sub-procedure deviating from a scheduled time period for the sub-procedure; and/or
a withdrawal of an interventional without deployment of the interventional device; and/or
a repeated deployment of an interventional device; and/or
a use of an alternate, secondary interventional device after using a primary interventional device; and/or
a parameter of the medical interventional imaging device or of an interventional device used during the interventional procedure.

14. The method according to claim 12,
wherein the step of detecting if an abnormal state occurs during the intervention comprises detecting the abnormal state based on interventional data.

15. A non-transitory computer-readable storage medium encoded with a computer program comprising a program code for causing a computer, when the computer program is run on the computer, to perform the method according to claim 12.

* * * * *